United States Patent [19]

Fisher

[11] Patent Number: 4,587,834
[45] Date of Patent: May 13, 1986

[54] METHOD AND APPARATUS FOR ANALYZING GASES DISSOLVED IN A LIQUID SAMPLE

[75] Inventor: David J. Fisher, North Adams, Mass.

[73] Assignee: General Electric Company, King of Prussia, Pa.

[21] Appl. No.: 709,253

[22] Filed: Mar. 7, 1985

[51] Int. Cl.⁴ .............................................. G01N 30/00
[52] U.S. Cl. ....................................... 73/23.1; 436/161
[58] Field of Search ................ 73/23.1, 19, 23; 55/67, 55/197, 386, 270, 159; 422/89; 436/60, 139, 141, 143, 154, 159, 161

[56] References Cited

U.S. PATENT DOCUMENTS

| 3,522,172 | 7/1970 | Pretorius et al. | 210/635 |
| 3,859,209 | 1/1975 | Jahnsen et al. | 73/23.1 |
| 3,881,892 | 5/1975 | Gehrke et al. | 55/67 |
| 3,988,919 | 11/1976 | Talmi et al. | 73/23.1 |
| 4,058,373 | 11/1977 | Kurz et al. | 73/19 |
| 4,112,737 | 9/1978 | Morgan | 73/23 |
| 4,236,404 | 12/1980 | Ketchum et al. | 73/19 |
| 4,402,211 | 9/1983 | Sugawara et al. | 73/19 |

Primary Examiner—Stephen A. Kreitman
Attorney, Agent, or Firm—Robert A. Cahill; William Freedman

[57] ABSTRACT

Automated gas chromatographic apparatus is utilized to analyze various gases dissolved in the insulating oil of an oil-filled power transformer in an expeditious and reliable manner. A sample of the insulating oil is introduced into a sample loop via a sampling valve, from which it is propelled by an inert carrier gas into a degassing chamber comprised of a vertically oriented tube packed with spherical packing elements. The carrier gas sweeping upwardly through this tube strips the various gases out of solution for conveyance by the carrier gas in plug flow fashion to a gas chromatograph where the stripped gases are separated and individually analyzed.

25 Claims, 4 Drawing Figures

METHOD AND APPARATUS FOR ANALYZING GASES DISSOLVED IN A LIQUID SAMPLE

The present invention relates to gas chromatography and, more particularly to a method and apparatus for extracting trace amounts of gases dissolved in electrical insulating liquids for qualitative and quantitative analysis.

It is now well recognized that the operating condition of liquid insulated electrical apparatus, such as oil-filled power transformers and reactors, can be determined with reasonable accuracy by determining what gases and their concentrations are dissolved in the insulating liquid, typically oil. It is known that certain gases, such as carbon monoxide and carbon dioxide are given off and dissolved in transformer oil as the result of thermal aging and degradation of the cellulosic insulation used in the transformer. High energy arcing in oil is known to produce large percentages of hydrogen and acetylene with lesser amounts of methane and ethylene. If the arc is associated with cellulose, significant amounts of carbon monoxide and carbon dioxide are released. Low energy spark discharges in oil produce hydrogen and some methane. Severe heating, a fault usually caused by a turn-to-turn winding failure or a poor electrical connection, results in thermal breakdown of the oil and the release of significant amounts of hydrogen, methane and ethylene. The release of predominant amounts of hydrogen and significant amounts of methane, with traces of ethane and ethylene is characteristic of corona discharges in the oil. Significant quantities of hydrogen are an indication of excessive moisture in critical areas of the transformer. All of these released gases dissolve to a greater or lesser degree in the transformer oil. Accurate analysis as to which gases and their concentration are dissolved in the transformer oil can thus provide an indication of the type of internal fault a transformer is or has experienced and, in many instances, a clue as to the location of the fault. Such indications are invaluable not only with regard to power transformers in service, but also during heat runs on new transformers to identify design and construction deficiencies. Periodic analysis of the gases will show their rates of release and thus provide indications of incipient faults and failure modes Early detection of these conditions buys sufficient time to plan an orderly shutdown of the transformer for maintenance and repair, thus averting a failure resulting in interruption of electrical service, as well as significant financial loss to the utility and manufacturer.

A number of proposals have been suggested and in some instance actually utilized for on-site analysis of the gases evolved by power transformers while in service. Examples of such proposals are disclosed in U.S. Pat. Nos. 4,058,373; 4,112,737; 4,236,404 and 4,402,211. Such on-site gas analysis approaches suffer from one or more of the following shortcomings: expensive to implement, inaccuracy, inability to detect and/or quantify all of the gases of interest, and low sensitivity. These shortcomings are significant, as concentrations of certain gases in concentrations of 10–20 parts per million or less are meaningful, particularly insofar as early incipient fault detection is concerned.

As a consequence, the most commonly accepted method for detecting and measuring gas emissions in oil-filled transformers is that set forth in American Society For Testing and Materials (ASTM) standard D-3612. As detailed therein, an oil sample is carefully extracted from the bottom drain valve of the transformer tank, and, without exposing it to the atmosphere, the sample is sent to a laboratory. The dissolved gases are then vacuum extracted and injected into a gas chromatograph to determine the presence and concentrations of the various gases of interest. Vacuum extraction of the dissolved gases from the transformer oil sample is an involved, time-consuming procedure necessarily conducted by trained personnel to insure the integrity of the analysis. The laboratory equipment required includes a vacuum pump, several flasks, a magnetic stirrer, a myria of tubes, numerous valves, and so forth. All of this equipment is cumbersome to operate properly and represents additional opportunity for error. When a sufficient quantity of gas is extracted from the oil sample, a measured sample thereof is withdrawn with a syringe and then injected into a gas chromatograph for analysis. The whole process from vacuum extraction to gas chromatograph readout requires an hour and a half for a single oil sample. Under these circumstances, a utility may have to wait a considerable length of time before obtaining the gas analysis results, leaving less time for undertaking the requisite measures to service a particular power transformer imminently in danger of failure.

It is accordingly an object of the present invention to provide an improved method and apparatus for performing gas chromatographic analysis of gases dissolved in a liquid.

An additional object is to provide a method and apparatus of the above-character wherein degassing of the liquid is achieved in an improved manner.

Another object of the present invention is to provide an improved method and apparatus for stripping gases from solution in an electrical apparatus insulating oil in a simplified and expeditious manner for subsequent qualitative and quantitative analysis.

A further object is to provide a method and apparatus of the above-character where the gases are stripped in a manner more conducive to accurate analysis by a gas chromatograph.

Yet another object is to provide a method and apparatus of the above character for analyzing the gases dissolved in transformer oil such as to determine the operating condition of a power transformer.

Other objects of the invention will in part be obvious and in part appear hereinafter.

SUMMARY OF THE INVENTION

In accordance with the present invention, there is provide an improved gas chromatographic apparatus and a method for operating same in order to expeditiously obtain a sample volume of gases from a sample volume of liquid in which the gases had been dissolved. The sample mixture of gases is then automatically injected into a gas chromatograph for qualitative and quantitative analysis. At the heart of applicant's invention is a unique degassing chamber into which a metered quantity of the liquid sample is injected. The gases dissolved in the liquid sample are literally stripped out of solution by the flow of an inert carrier gas through the chamber. The stripped gases are swept by the carrier gas out of the degassing chamber in plug flow fashion and into a gas chromatograph for analysis. The degassing chamber comprises, in accordance with a preferred embodiment of the present invention, a vertically oriented, elongated stainless steel tube packed approximately one-third full with spherical elements, such as steel shot, to present a large surface area over which the liquid sample clings as a thin film. The diameters of the lower inlet first admitting the liquid sample and the carrier gas into the tube and the upper outlet through which the carrier gas and the stripped gases flow preferably are of a ratio of approximately 1:5 relative to the tube inner diameter to minimize carrier gas turbulence within the tube. The carrier gas sweeping through the tube reduces the partial pressures for the gases at the surfaces of the liquid coated packing elements, thus pulling the gases out of solution in accordance with Henry's Law. The liquid coated packing elements greatly increase the liquid surface area, and this coupled with the agitation and bubbling of the carrier gas through any liquid pooled in the tube provides for highly efficient extraction of the gases from the liquid sample. As a result, the extracted gases are swept out of the tube in plug flow fashion for injection into the gas chromatograph. The detector signal pattern generated by the gas chromatograph thus will exhibit sharp, high amplitude peaks for each constituent gas in the gas sample, rendering the analysis results more readily interpretable.

In the disclosed embodiment of the invention, the liquid sample is an insulating oil sample taken from an oil-filled electrical apparatus, such as a large power transformer. Analysis of the gases extracted from the oil sample provides an indication of the operating condition of the electrical apparatus from which the oil sample is as taken.

The invention accordingly comprises the features of construction, combination of elements, arrangement of parts and series of method steps which will be exemplified in the description hereinafter set forth, and the scope of the invention will be indicated in the claims.

For a fuller understanding of the nature and objects of the invention, reference should be had to the following detailed description taken in connection with the accompanying drawings, in which.

Like reference numerals refer to corresponding parts throughout the several view of the drawings.

DETAILED DESCRIPTION

Figure 1:
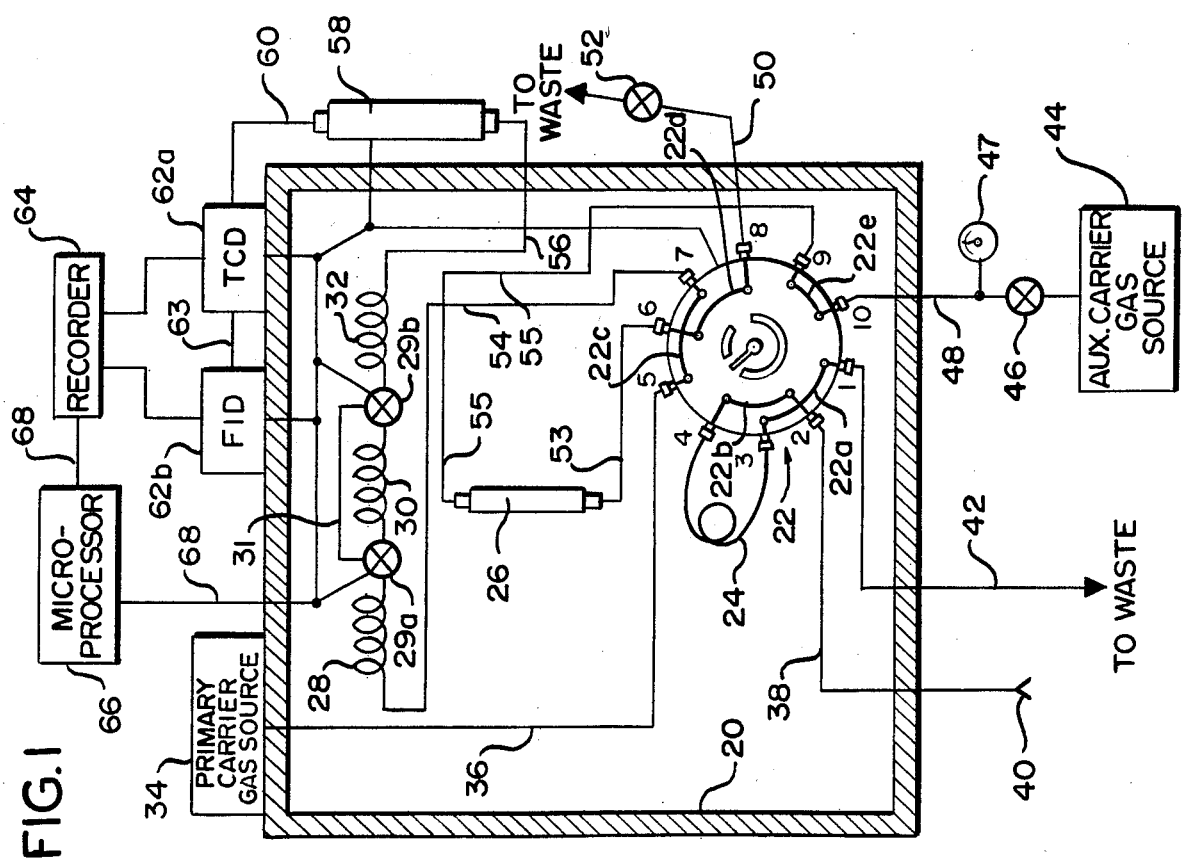
FIG. 1 is a schematic diagram of a gas chromatographic apparatus constructed in accordance with the present invention and shown in its fill and back flush condition.
Figure 4:
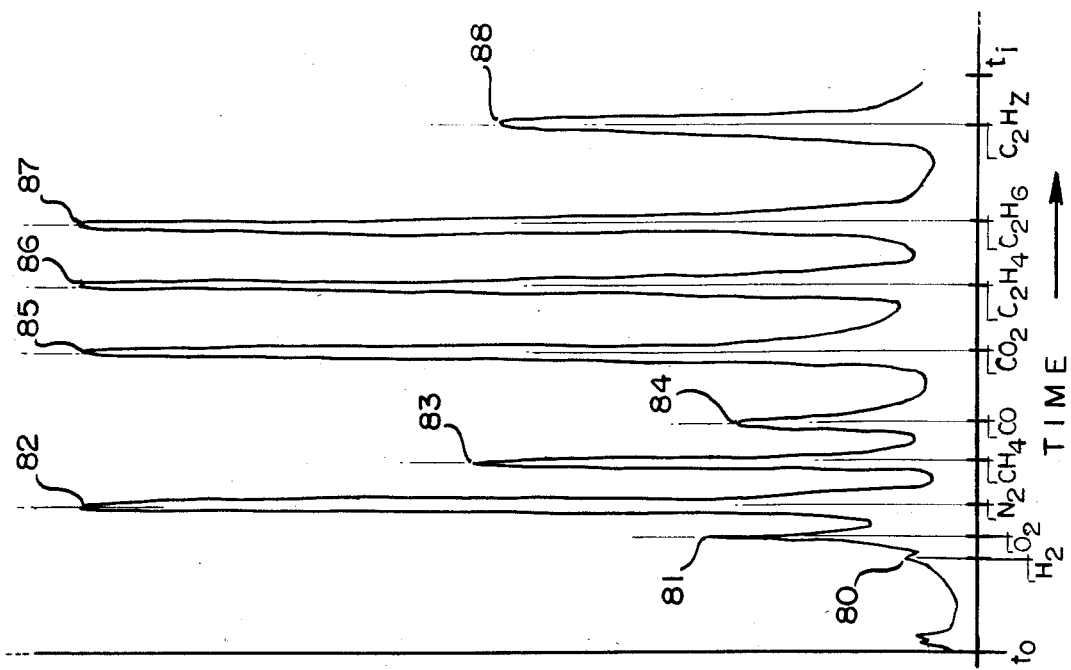
FIG. 4 is a illustration of a typical chromatogram of a gas analysis obtained using the apparatus of FIG. 1.

The gas chromatographic apparatus of the present invention, as seen in FIG. 1, is for the most part contained within an enclosure 20 whose interior is held at a constant temperature environment of, for example, 70° C. The major components disposed within this enclosure are a ten port fluid sampling valve, generally indicated 22, a sample loop 24, a degassing chamber 26, and a series of gas separating columns indicated at 28, 30 and 32. The sample loop is connected between ports 3 and 4 of the sampling valve, while the degassing chamber is connected between ports 6 and 9. An external source 34 of a suitable primary carrier gas, preferably argon, is connected by tubing 36 to port 5 of the sampling valve. Port 2 is connected by tubing 38 exiting enclosure 20 to a conventional gas chromatographic injection port, indicated schematically at 40, where an oil sample contained in a syringe (not shown) is injected into the apparatus. Tubing 42 connected with sampling valve port 1 is brought out from the enclosure to an oil waste sump (not shown). An auxiliary carrier gas source 44 is controllably supplied via a valve 46 and tubing 48 to port 10 of the sampling valve. Port 8 thereof is coupled externally of the enclosure to waste via tubing 50 and an inline restrictor valve 52. Port 6 is connected via tubing 53 to the lower end of degassing chamber 26, with the upper end thereof connected by tubing 55 to port 9 of sampling valve 22. Finally, sampling valve port 7 is connected by tubing 54 to one end of the series of gas separating columns 28, 30, 32, with the other end thereof connected by tubing 56 to an external converter 58, which, in turn, is connected by tubing 60 to a gas chromatograph detectors 62a and 62b serially connected by tubing 63. The electrical readouts of these detectors are fed to a recorder 64 to create a chromatogram such as illustrated in FIG. 4. As shown, column 30 is selectively shunted out of the circuit by valves 29a, 29b and tubing 31, for reasons discussed below. The operations of the various valves, detectors, recorder 64 and converter 58 are coordinated in time by a microprocessor 66 via electrical connections thereto commonly indicated at 68.

In the sampling valve position illustrated in FIG. 1, which is the fill and back flush condition of the gas chromatographic apparatus, ports 1 and 3 are interconnected by a valve coupling 22a, ports 2 and 4 by a valve coupling 22b, ports 5 and 7 by a valve coupling 22c, ports 6 and 8 by a valve coupling 22d, and ports 9 and 10 by a valve coupling 22e. As a result of this sampling valve position, it is seen that sample loop 24 is connected in series between oil sample injection port 40 and oil sample waste at the external terminus of tubing 42. Thus, an oil sample can now be injected into port 40, and when oil is observed exiting tubing 42, a know volume of the oil sample is contained in sample loop 24. Injection of eight mililiters of oil has been found sufficient to flush and fill the sample loop.

Meanwhile, the sampling valve is in a position to route auxiliary carrier gas downwardly through degassing chamber 26 and out through tubing 50 to waste. This carrier gas flow through the degassing chamber is for the purpose of back flushing the chamber to substantially remove the previous oil sample. Also during this time, primary gas from source 34 flows through the gas separator columns 28, 30, 32, converter 58, and detectors 62a, 62b to establish a baseline response for the gas chromatograph, which may be a GC-9APTF microprocessor-controlled gas chromatograph available from Shimadzu Scientific Instruments Inc. of Columbia, MD. A suitable microprocessor 64 is a C-R2AX data processor available from the same source. Sampling valve 22 may be sourced from Valco Instruments Co. of Houston, TX.

Figure 2:
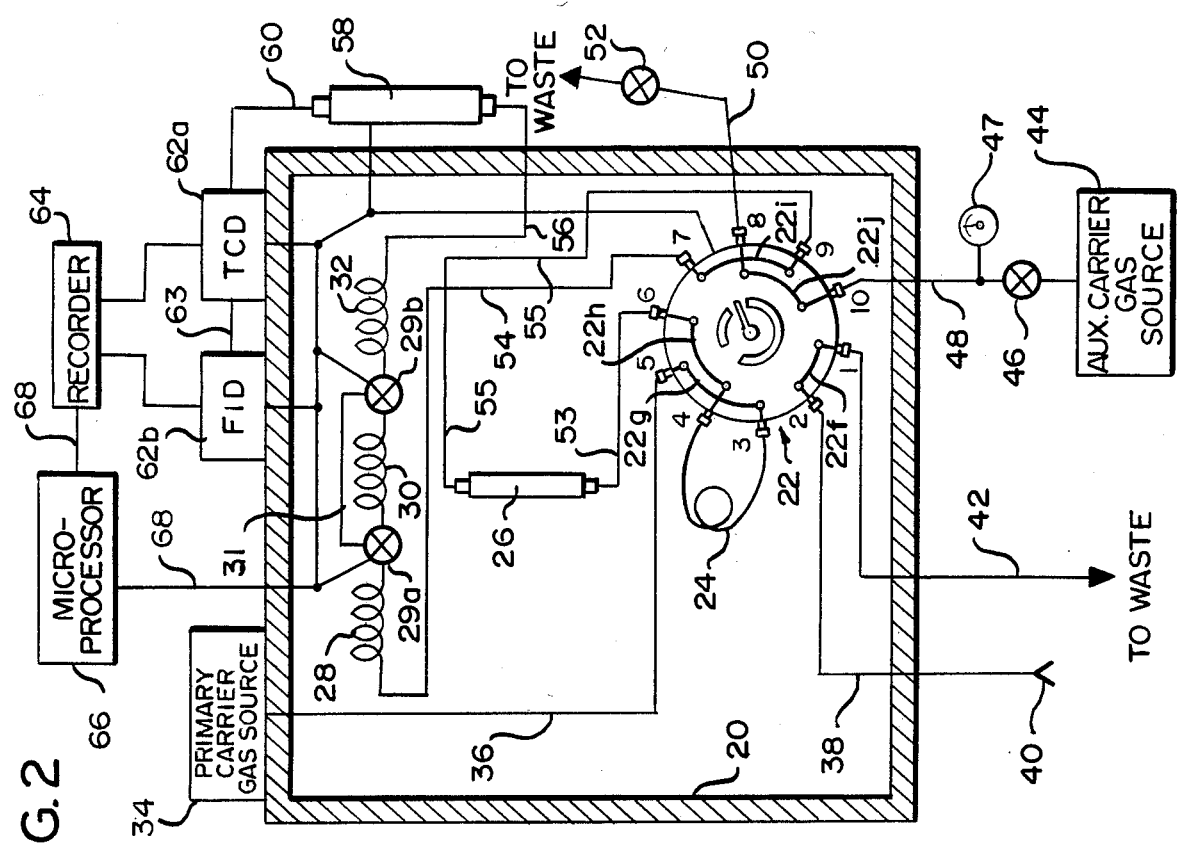
FIG. 2 is a schematic diagram of the gas chromatographic apparatus of FIG. 1, shown in its sample injection condition.

Turning to FIG. 2, the apparatus of FIG. 1 is shown with sampling valve 22 in its gas chromatograph injection position, as conditioned by microprocessor 66. Thus, oil sample input and output tubings 38 and 42 are interconnected by sampling valve coupling 22f. Ports 3 and 5 are now interconnected by valve coupling 22g and ports 4 and 6 are interconnected by valve coupling 22h, with the result that the oil sample in sample loop 24 is forced by the primary carrier gas into vertically oriented degassing chamber 26 through its bottom inlet. The upper outlet end of the degassing chamber is now connected via sampling valve coupling 22i to the series of gas separator columns 28, 30, 32, and thus gases drawn out of solution in the oil sample by the primary carrier gas sweeping through the degassing chamber are conveyed in plug flow fashion, again by the primary gas, to the gas chromatograph for analysis. Finally, the sampling valve coupling 22j simply conveys the auxiliary carrier gas to waste; the restrictor valve 52 being regulated with reference to pressure gauge 47 to present the same flow rate restriction the auxiliary carrier gas experienced while backflushing the degassing chamber (FIG. 1).

Figure 3:
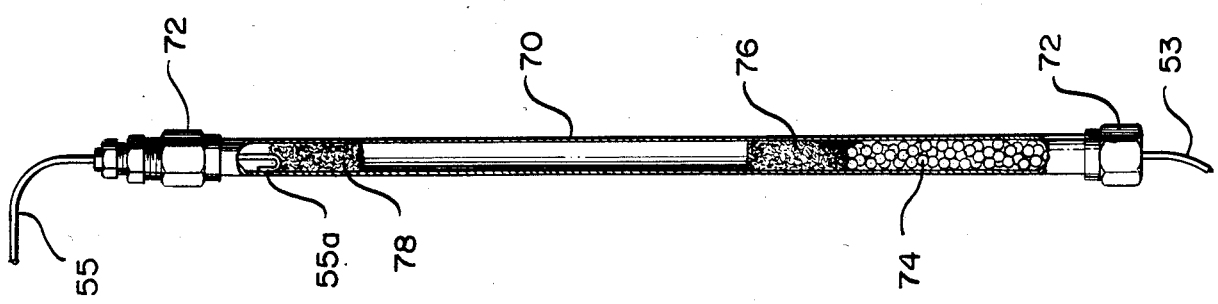
FIG. 3 is an elevation view, partially in section, of the degassing chamber utilized in the gas chromatographic apparatus of FIG. 1.

Turning now to FIG. 3, the degassing chamber 26 is, in accordance with the present invention, comprised of an elongated, metallic tube 70, for example a standard quarter inch outer diameter, stainless steel tube approximately nine inches long. The ends of this tube are equipped with appropriate fittings 72 to sealingly introduce tubing 53 into the bottom of the tube and tubing 55 into the top. This tubinq is preferably standard one-sixteenth inch OD tubing, such that the ratio of the tube 70 and tubing 53, 55 inner diameters is approximately 5:1 to afford efficient, non-turbulent carrier gas stripping action. Thus, the tube and tubing ID's may be varied, as long as the approximate 5:1 ratio is maintained. The interior surface of tube 70 should be somewhat rough to promote retention of an oil film thereon, and it has been found that a standard $\frac{1}{4}$ inch stainless steel tube has adequate interior surface roughness to fulfill this purpose without additional processing.

In my prior work leading up to the present invention, I had proposed to utilize an empty stainless tube of the type thus far described above as a degassing chamber in gas chromatographic apparatus basically as shown in FIGS. 1 and 2. It was found however that the analysis response of the gas chromatograph to a standard gas mixture of known constituent concentrations pursuant to a calibration run differed significantly from the response obtained from a gas mixture which had been extracted from an oil sample injected into the degassing chamber. That is to say, the gas chromatograph detector response characteristics for the various gases of concern inexplicably differed, depending upon whether these gases were introduced into the empty degassing tube already in their vapor state or while dissolved in oil. This situation made it extremely difficult to enter the appropriate correction factors and thus calibrate the gas chromatograph so that the responses to gases of unknown concentrations extracted from an oil sample could be conveniently interpreted and quantified.

I have discovered that this problem is conveniently and effectively overcome by packing tube 70 to approximately one-third its length, i.e., height, with spherical packing elements effective in presenting a large surface area on which an oil sample injected via tubing 53 can cling as a thin film. While non-porous, etched surface beads of glass or polymeric materials may be used as packing elements, I have found that steel shot 74 of 10-20 mesh size (1/16-$\frac{1}{8}$ inch diameter) is imminently suitable as packing elements for purposes of the present invention. To retain the steel shot in place in the bottom third of tube 70, a porous glass wool plug 76 is utilized. A second porous glass wool plug 78 is positioned adjacent the top of the tube and serves to break up any oil bubbles entrained by the primary carrier gas sweeping upwardly through the tube. Also, the end portion of tubing 55 within the upper end of the degassing tube is bent back on itself in the fashion of a button hook, as indicated at 55a, as further assurance against the entry of oil into the tubing and conveyance by the carrier gas on to the gas separator columns, which, if permitted to occur, would destroy the efficacy of the molecular sieve material therein.

While the reasons for the achieved uniformity of gas chromatographic detector responses to a standard gas mixture injected into degassing tube 70 and the same gas mixture dissolved in an oil sample introduced into the degassing tube is not fully understood, it is believed that the fact that the steel shot 74 takes up substantial dead space within the tube is a significant factor. Non-turbulent flow of the carrier gas is thus further assured. Moreover, the dramatic increase in the oil surface area, by virtue of its coating the surfaces of the steel shot, as well as the tube interior surface and the glass wool plugs, affords a significant increase in the degassing efficiency of the carrier gas sweeping past. Consequently a higher percentage of the total concentration of the gases are stripped out of solution in less time. Thus, the stripped mixture of gases is swept out of the degassing tube by the carrier gas as a more discrete volume or plug for introduction into the gas separating columns of the gas chromatograph. Such plug flow of the stripped gases closely resembles the flow characteristics of a standard gas mixture being propelled by the carrier gas out of the sample loop and through the degassing tube to the separating columns. It should be noted that, for the sake of simplicity, provisions for conducting such a calibration run with a standard gas mixture have been omitted from the apparatus of FIGS. 1 and 2. It should also be noted that, while highly efficient carrier gas stripping is achieved in degassing tube 70, the full concentrations of each of the gases are not pulled out of solution during a sample run. However, by analyzing the gases stripped from a standard oil sample of known dissolved gas concentrations by carrier gas of a given flow rate during a predetermined optimum time frame, appropriate correction factors can be readily determined and applied to the gas chromatograph detector responses by microprocessor 66 to provide a highly accurate determination of the actual concentrations of the various gases originally dissolved in an unknown oil sample.

In determining the operating condition of oil-filled power transformers, there are nine gases, the concentrations, if any, of which dissolved in the oil samples are of interest. These nine gases are hydrogen, oxygen, nitrogen, methane ($CH_4$) carbon monoxide, carbon dioxide, ethylene ($C_2H_4$), ethane ($C_2H_6$), and acetylene ($C_2H_2$). Returning to FIG. 2, the argon primary carrier gas, flowing at a preferred rate of 30-40 cc/min., sweeps through degassing chamber 26 and strips these gases from the oil sample introduced therein. The stripped gases are swept out of the top of the degassing chamber as a rather discrete gas mixture slug for plug flow through sampling valve 22 to the series of gas separator columns 28, 30, and 32. As is well understood in the art of gas chromatography, these columns contain differing types of molecular sieve and porous polymer materials intended to separate the various gases of a mixture flowing therethrough on the basis of their relative molecular weights. That is, as is well understood in the art, the flow rates of the various gas are selectively and differentially retarded in accordance with their molecular weights and configurations. Thus, in accordance with the present invention, the first column 28 of the series is designed such that, of the nine gases of interest entering this column as a discrete mixture, the lightest five, namely $H_2$, $O_2$, $N_2$, $CH_4$ and CO, exit as a group, while the remaining four, namely, $CO_2$, $C_2H_4$, $C_2H_6$ and $C_2H_2$ exit in staggered time relation, i.e., separated in time. The second column 30 is designed to separate the grouped mixture of the five lightest gases exiting first from column 28, and these separated gases then flow successively through column 32 which is designed to preserve their time separated status. In the interval between the exiting of the last (CO) of the separated first five gases from column 30 and the arrival of the first ($CO_2$) of the last four gases at the entry of column 30, valves 29a and 29b are operated by microprocessor 66 to switch this column out of the circuit via shunting tubing 31. Thus the last four gases exiting column 28 flow directly to column 32, which is specifically designed to impart greater separation to the last two gases, namely $C_2H_6$ and $C_2H_2$, than was created in column 28.

From column 32, the separated gas flow through converter 58 to detector 62a which, in accordance with the invention, is a thermal conductivity detector (TCD) of known construction. A TCD detector is utilized herein because it is a known viable form of detection means for detecting the presence and concentrations of $H_2$, $O_2$ and $N_2$, the first three of the nine separated gases exiting column 32. Having determined the operating characteristics of the degassing chamber and the gas separating columns, knowing the primary carrier gas flow rate and the instant in time sampling valve 22 is operated from its FIG. 1 fill and back flush position to its FIG. 2 injection position, the arrival of the various gases at various points in the gas chromatographic fluid circuit can be accurately predicted. Microprocessor 66 can thus be readily programmed to control the operations of the various components in proper timing and sequence so as to obtain the gas analysis chromatogram of FIG. 4 on an essentially automated basis. Thus, valves 29a and 29b are operated at the proper times under microprocessor control to shunt the last four gases around column 30. At the predicted arrival times of the first three gases, $H_2$, $O_2$ and $N_2$, at TCD detector 62a, it is activated by the microprocessor to detect the presence thereof and indicate their concentrations. Referring to the chromatogram of FIG. 4 created by recorder 64, representative responses to these three gases are illustrated by the peaks 80, 81 and 82; the areas under these peaks representing their concentrations.

The remaining six gases are best analyzed by flame ionization detector (FID) 62b connected downstream of the TCD detector by tubing 63. Thus, just prior to the arrival of the fourth gas, $CH_4$, the FID detector is activated by the microprocessor to look for this gas, and a representative response thereto is illustrated by peak 83 in FIG. 4. It is known that best procedure for accurately measuring the concentrations of carbon monoxide and carbon dioxide using a FID detector is to convert these gases to methane $CH_4$. Thus, after the methane gas extracted from the oil sample has exited converter 58, commonly known as a catalytic methanator, it is activated by the microprocessor during a time frame bracketing the passage of the next two gases, CO and $CO_2$, through the converter. Hydrogen is introduced into converter 58, and first CO and then $CO_2$ are burned to convert these carbonaceous gases to $CH_4$. These two slugs of $CH_4$ flow in succession to FID detector 62b for analysis. Peaks 84 and 85 in FIG. 4 illustrate the FID detector responses to these two $CH_2$ slugs scaled by the microprocessor to represent the concentrations of CO and $CO_2$. Finally, the last three gases, ($C_2H_4$, $C_2H_6$ and $C_2H_2$) arrive in succession at the FID detector, with the detector responses thereto being illustrated by peaks 86, 87 and 88 in the chromatogram of FIG. 4. By way of example, the time required to create this chromatogram, time $t_0$-$t_1$, is approximately 19 minutes. It is seen that the detector response peaks are well defined and amply spaced apart, thus rendering the chromatogram generated by the gas chromatographic apparatus of the present invention readily interpretable.

It has been experimentally determined that the optimum oil sample degassing duration is approximately 1.5 minutes, beginning at the moment the sampling valve is converted from its FIG. 1 position to its FIG. 2 position. Thus, even before the first gas, hydrogen, arrives at detector 62a, the microprocessor switches sampling valve 22 back to its FIG. 1 fill and backflush position. Primary carrier gas then bypasses the degassing chamber and is routed directly to the separating columns to continue driving the stripped gases therethrough. Thus the minor concentrations of any gases left in the oil sample at the end of the 1.5 minute degassing interval are not introduced into the gas chromatograph, and can not therefore contaminate the gas sample being analyzed. That is, analysis is performed strictly on the basis of the concentrations of the nine gases of interest extracted from the oil sample during the time frame of the degassing interval.

While the chromatogram of FIG. 4 is being generated by the recorder 64, auxiliary carrier gas is now routed into the top end of degassing chamber 26 and thus sweeps downwardly through vertically oriented tube 70 (FIG. 3), thereby effectively purging the substantially degassed oil sample from the interior tube surfaces, the glass wool plugs and the steel shot. The purged oil sample exits the bottom of the degassing chamber and is routed to waste via sampling valve 22 and tubing 50. It will be appreciated that the vertical orientation of the degassing chamber contributes both to the efficiency of the oil sample degassing process, when primary carrier gas sweeps upwardly therethrough, and to the effectiveness of the oil sample purge, back flush operation, when auxiliary carrier gas sweeps downwardly therethrough. Also during the back flushing operation, sample loop 24 is isolated from the primary and auxiliary carrier gas flows and thus is available to receive the next oil sample.

From the foregoing description, it is seen that, by virtue of the present invention, analysis of the gases dissolved in an oil sample is performed expeditiously in an essentially automated fashion. Measured from the moment the oil sample is introduced into the degassing chamber to the completion of a chromatogram for the indicated nine gases of interest, a complete analysis is performed in approximately twenty minutes. Compared to the approximately ninety minutes to complete an analysis when using traditional vacuum extraction techniques to extract the gas sample from the oil sample, it is seen that the present invention affords dramatic time savings. The only manual operation required by the present invention is the introduction of the oil sample into the sample loop, the rest is automated under the control of the microprocessor. Thus the possibility of sample contamination is reduced to a minimum, thereby guaranteeing more reliable, accurate results as compared to prior art approaches.

It will be appreciated that, while the present invention has been disclosed in the context of analyzing of specific gases dissolved in an insulating oil sample drawn from an oil-filled power transformer, the principles disclosed herein may be applied to the analysis of gases dissolved in liquids generally.

It will thus be seen that the objects of the invention set forth above and made apparent from the foregoing description are efficiently attained and, since certain changes may be made therein without departing from the scope of the invention, it is intended that all matter contained in the above description or shown in the accompanying drawings shall be interpreted as illustrative and not in a limiting sense.

Having described my invention, what I claim as new and desire to secure by Letters Patent is:

1. Gas chromatographic apparatus for analyzing gases dissolved in a liquid, said apparatus comprising, in combination:
   a. means for holding a predetermined volume of the liquid as a liquid sample;
   b. a gas chromatograph for qualitatively and quantitatively analyzing the gases dissolved in said liquid sample;
   c. a source of primary carrier gas;
   d. a degassing chamber comprising a vertically oriented, elongated tube having openings in its upper and lower ends and containing a number of discrete packing elements, and
   e. means for connecting said holding means and said degassing chamber in series between said primary carrier gas source and said gas chromatograph, whereby said primary carrier gas forces said liquid sample from said holding means into said tube via said lower end opening thereof where it forms a surface coating on said packing elements, said primary carrier gas sweeping upwardly through said tube to extract the gases from solution in said liquid sample, said extracted gases being propelled by said primary carrier gas from said tube via said upper end opening thereof to said gas chromatograph for analysis.

2. The gas chromatographic apparatus defined in claim 1, wherein said tube further contains a porous plug for confining said packing elements to the lower portion of said tube.

3. The gas chromatographic apparatus defined in claim 2, wherein said packing elements are of a spherical shape.

4. The gas chromatographic apparatus defined in claim 3, wherein said packing elements are steel shot of 10-20 mesh size.

5. The gas chromatographic apparatus defined in claim 2, which further includes a source of auxiliary carrier gas, said connecting means being operable to route said auxiliary carrier gas downwardly through said tube to waste after said gases have been extracted from said liquid sample during a degassing internal of predetermined time duration whereby to purge said tube of said liquid sample.

6. The gas chromatographic apparatus defined in claim 5, wherein the ratio of the diameter of said tube to the diameters of said upper and lower end openings into said tube is approximately 5:1.

7. The gas chromatographic apparatus defined in claim 5, wherein said packing elements are of a spherical shape and 10-20 mesh size, said liquid sample is insulating oil taken from an oil-filled electrical apparatus, and said degassing interval duration is limited to approximately 1.5 minutes.

8. The gas chromatographic apparatus defined in claim 7, wherein said gas chromatograph includes a series of gas separator columns, a catalytic methanator, a thermal conductivity detector and a flame ionization detector through which said primary carrier gas and said extracted gases flow in succession.

9. The gas chromatographic apparatus defined in 7, wherein said primary carrier gas flows at the rate of 30-40 cubic centimeters per minute.

10. Gas chromatographic apparatus for analyzing gases dissolved in a liquid, said apparatus comprising, in combination:
   a. a sampling valve movable between first and second valve positions;
   b. a sample loop connected by said sampling valve in said first valve position to accept a predetermined volume of the liquid as a liquid sample;
   c. a gas chromatograph for qualitatively and quantitatively analyzing the gases dissolved in said liquid sample;
   d. a source of primary carrier gas, said sampling valve in said first position routing said carrier gas directly to said gas chromatograph to establish a baseline response therefor;
   e. a degassing chamber comprising a vertically oriented, elongated tube having openings in its upper and lower ends and containing a number of discrete packing elements, said sampling valve in said second valve position connecting said sample loop in series between said primary carrier primary gas source and said opening in the lower end of said tube and said opening in the upper end of said tube to said gas chromatograph, whereby said carrier primary gas forces said liquid sample from said sample loop into said tube where it forms a surface coating on said packing elements, said primary carrier gas sweeping upwardly through said tube to extract the gases from solution in said liquid sample, said extracted gases being propelled by said primary carrier gas from said tube to said gas chromatograph for analysis; and
   f. means for controlling the operation of said gas chromatograph and the positioning of said sampling valve between said first and second valve positions.

11. The gas chromatographic apparatus defined in claim 10, wherein said tube further contains a porous plug for confining said packing elements to the lower portion of said tube.

12. The gas chromatographic apparatus defined in claim 11, wherein said packing elments are of a spherical shape.

13. The gas chromatographic apparatus defined in claim 12, wherein said packing elements are steel shot of 10-20 mesh size.

14. The gas chromatographic apparatus defined in claim 11, which further includes a source of auxiliary carrier gas, said sampling valve in said first valve position routing said auxiliary carrier gas downwardly through said tube to waste, whereby to purge said tube of said liquid sample.

15. The gas chromatographic apparatus defined in claim 14, wherein the ratio of the diameter of said tube to the diameters of said upper and lower end openings into said tube is approximately 5:1.

16. The gas chromatographic apparatus defined in claim 14, wherein said liquid sample is insulating oil taken from an oil-filled electrical apparatus, and said control means limits the duration said sampling valve is in said second valve position to approximately 1.5 minutes.

17. The gas chromatographic apparatus defined in claim 16, wherein said gas chromatograph includes a series of gas separator columns, a catalytic methanator, a thermal conductivity detector and a flame ionization detector through which said primary carrier gas and said extracted gases flow in succession.

18. The gas chromatograph in apparatus defined in claim 17, wherein there are three gas separator columns in said series, said gas chromatograph further including valve means controlled by said control means to shunt certain ones of said extracted gases around an intermediate one of said gas separator columns.

19. The gas chromatographic apparatus defined in 14 wherein said primary carrier gas flows at the rate of 30–40 cubic centimeters per minute.

20. A method of analyzing the gases dissolved in an insulating oil sample taken from an oil-filled electrical apparatus, said method comprising the steps of:
   a. introducing a known volume of said oil sample into a sample loop via a sampling valve in a first valve position;
   b. switching the sampling valve to a second valve position to connect the sample loop in series between a source of primary carrier gas and the lower end of an elongated vertically oriented tube;
   c. flowing the primary carrier gas through the sampled loop at a rate of 30–40 cc/min. to propel the oil sample into the lower end of the tube where it is deposited as a film on the spherical surfaces of 10–20 mesh packing elements confined in the lower portion of the tube;
   d. continuing the flow of primary carrier gas upwardly through the tube for a duration of approximately 1.5 minutes to extract the gases from the oil sample deposited on the packing element surfaces and to convey the extracted gases in plug flow fashion out the upper end of the tube and via the sampling valve in its second valve position to the input of a gas chromatograph;
   e. switching the sampling valve back to its first valve position to route the flow of the primary gas directly to the gas chromatograph input whereby to convey the extracted gas through the gas chromatograph where they are separated and analyzed; and
   f. flowing a backflushing gas via the sampling valve in its first position downwardly through the tube to purge the oil sample therefrom.

21. The method defined in claim 20, which further includes the step of flowing the primary carrier gas directly through the gas chromatograph while the sampling valve is in its first position, whereby to establish a baseline response for the gas chromatograph.

22. The method defined in claim 20, wherein the gas chromatograph includes a series of three gas separator columns, a catalytic methanator, a thermal conductivity detector and a flame ionization detector through which the extracted gases and the primary carrier gas flow in succession, said method further including the step of shunting certain ones of the extracted gases around the second one of the series of gas separator columns.

23. The method defined in claim 22, wherein the extracted gases may include hydrogen, oxygen, nitrogen, methane, carbon monoxide, carbon dioxide, ethylene, ethane and acetylene, said method further including the steps of:
   a. detecting the presence of hydrogen, oxygen and nitrogen using the thermal conductivity detector; and
   b. detecting the presence of the remaining gases using the flame ionization detector.

24. The method defined in claim 23, wherein said shunting step diverts the gases carbon dioxide, ethylene, ethane, and acetylene from the second one of the series of three gas separator columns.

25. The method defined in claim 23, which further includes the step of converting the gases carbon monoxide and carbon dioxide to methane in the catalytic methanator.

* * * * *